United States Patent [19]

Burton et al.

[11] 4,076,701

[45] Feb. 28, 1978

[54] TUMOR COMPLEMENT FRACTION RECOVERY METHOD AND PRODUCT

[75] Inventors: Lawrence Burton, Commack; Frank Friedman, New York, both of N.Y.

[73] Assignee: Immunology Research Foundation, Inc., Great Neck, N.Y.

[21] Appl. No.: 600,027

[22] Filed: Jul. 29, 1975

[51] Int. Cl.² ............................................... A23J 1/06
[52] U.S. Cl. .......................... 260/112 B; 23/258.5 R; 210/DIG. 23
[58] Field of Search ...................... 260/112 R, 112 B; 23/258.5 R; 210/DIG. 23

[56] References Cited

U.S. PATENT DOCUMENTS 3,657,116  4/1972  Haller .......................... 210/DIG. 23
3,823,126  7/1974  Bjorklund ...................... 260/112 B Primary Examiner—Paul R. Michl
Attorney, Agent, or Firm—Barry Kramer

[57] ABSTRACT

A process is provided for the isolation of a blood polypeptide fraction or derivatives thereof herein termed the "tumor complement fraction" or "TCF", from mammalian blood. The process comprises a series of centrifugal separations of blood fractions under conditions which maintain the integrity of the desired material as it existed in vivo.

The Tumor Complement Fraction, is a new material and it constitutes another aspect of the disclosure. Isolated TCF, a natural polypeptide or derivative thereof, is useful as a neoplastic tissue remission and prevention agent.

11 Claims, No Drawings

TUMOR COMPLEMENT FRACTION RECOVERY METHOD AND PRODUCT

RELATED APPLICATIONS

Applicants are filing concurrently herewith several applications relating to the present invention and identified by their titles which are as follows:
1. Blocking Protein Fraction Recovery Method And Product, Ser. No. 600,028 filed July 29, 1975; and
2. Deblocking Protein Fraction Recovery Method and Product, Ser. No. 600,026 filed July 29, 1975

FIELD OF THE INVENTION AND PRIOR PUBLICATIONS

The present invention relates to a method for isolating a specific fraction of mammalian blood. It relates further to the provision of a composition which can be administered as a tumor remission agent, to tumor bearing mammals and which causes tumor tissue to undergo necrosis soon after the agent is administered. It relates further to a composition which can be administered to prevent tumor formation in healthy mammals.

The inventors have published the following articles, relating to the field of this invention:
1. Annals of The New York Academy of Sciences, Vol. 100, Part II, pages 791 – 814 (1963)
2. Pigment Cell Biology, pages 279 – 299, Academic Press, 1959
3. Transactions of The New York Academy of Sciences, Ser. II, Vol. 25, pages 29 – 32 (Nov. 1962)

BACKGROUND OF THE INVENTION

The quest for a cure for cancer has involved the expenditure of billions of dollars for research, millions of scientist hours of effort, the construction of institutions devoted to the problem and generation of a body of literature, and yet, not even the nature of the problem, let alone its solution, has been discovered.

Approaches to the seemingly neverending search have fallen into three general categories: Surgical, radiological and chemotherapeutic. Each has a modicum of success for treating certain types of tumors. Surgery, for example, can completely cure breast cancer if the operation is properly performed in the early stages of tumor growth, but will only temporarily prolong life if performed when the tumor is in advanced stages of growth. Even if breast cancer is cured by complete removal of tumor cells and the surrounding tissue, there are self-evident disadvantages to this approach.

Radiological and chemical treatment of cancer cells reduces mitotic division of cancer cells and thus reduces, if not completely inhibits the rate of tumor growth, but such treatments have several distinct and widely known disadvantages. In the first place, neither treatment is selective only to cancer cells; they damage both healthy and tumor cells. Radiological treatment is generally useful only when the tumor cells are in a relatively localized state, since any attempt to treat the body generally to control widely dispersed cancer cells would inflict great damage on the healthy cells of the host animal. Known chemotherapeutic agents such as the nitrogen mustards, because of their destructive side effects are considered a treatment of last resort to be used only when other treatments have failed.

The present invention relates to a new chemotherapeutic approach to the treatment of cancer. The problems in attempting to find a chemotherapeutic cancer cure are manifold because the chemistry of the onset of cancer is as complex as life itself. Prior investigators have generally concentrated their efforts on the development of "synthetic" chemotherapeutics, i.e., extracorporeal chemicals. Massive programs, sponsored by both governmental and private agencies, have been set up to screen old and new chemicals for anti-tumor activity and tens of thousands of chemicals have been thus examined, but to date, a cancer cure has not been discovered.

SUMMARY OF THE INVENTION

The present inventors have proceeded in their quest for a chemotherapeutic means to reduce or inhibit tumor growth, on several assumptions. One assumption is that mammals have within their blood one or more growth components which control cell division (mitosis) and growth, i.e., an anticancer immune defense mechanism (IDMC). A second assumption is that a balanced proportion of these components leads to normal cellular mitosis and growth; whereas, an imbalance leads to malignant neoplasms, i.e., malignant tumors. The third assumption is that these growth components can be isolated from blood, without deactivating them, more easily than they could be synthesized. And the fourth assumption was that administration of such growth components to a tumor bearing mammalian host would result in reduction and/or remission of neoplasmic tissue formation, i.e., cause the hosts' natural IDMC to function.

The theories upon which the present invention are based are not inconsistent with immunologic theories that the immune system can defend the body from cancer, provided the system itself is not impaired. However, theoretical considerations do not cure, and the incomprehensible complexity of IDMC or some other host disease defense mechanism has until now prevented its reduction to practice. The problem is that in the process of extracting and handling biologic materials away from their in vivo environment, it is difficult to avoid the traumatic effect of the extraction process on the material itself. All steps of the extraction and handling processes had to be governed by the imperative that the extracted material had to be preserved as it existed in vivo, with as little alteration or damage as possible.

Since the materials which were sought were unknown in structure, although it could be presumed that they were polypeptides or proteins or derivatives thereof, the success of each step in following this imperative had to be determined emperically, i.e., by trial and error.

For example, if a fraction of a mouses's blood is injected into a tumor bearing mouse, and the tumor does not respond, then the blood fraction may be centrifuged to give a sediment and a supernatant, each of which is again tested on tumor bearing mice. If, again, the tumors do not respond, then perhaps the blood fraction is centrifuged at a higher speed. If, for example, the resultant sediment is injected and causes a positive response, then it is clear that centrifuging at the higher speed resulted in the separation of a tumor controlling component. Also to be considered is the question "What is in the supernatant that, before being separated from the active sediment, inhibited the tumor activity of the material in the sediment."

Proceeding in the foregoing fashion, the inventors were able to isolate three blood components or fractions, the presense in balanced proportion of which, both inhibits the formation, and causes the necrosis of neoplasmic tissue. These components are virtually non-toxic and have no apparent side effects or adverse effect on normal tissue. The toxicity is so minimal that an L.D. 50 has thus far not been obtainable.

Though the chemical structure of the useful blood components has not been illucidated, it being only known that they are proteins or polypeptides or derivatives thereof, the materials have been identified and named as follows:

1. Tumor Complement Fraction ("TCF") a peptide chain or derivative thereof that attacks a tumor and causes necrosis of the tumor tissue
2. Blocking Protein Fraction ("BPF") a substance that blocks the activity of TCF
3. Deblocking Protein Fraction ("DPF") a protein or derivative thereof that neutralizes or "de-blocks" BPF TCF, BPF, and DPF must be in balance to maintain a tumor-free condition. In a normal animal, tumor growth is prevented by the presence of a greater amount of TCF than BPF. In a tumor-bearing animal, less TCF is present in the blood. By administering DPF to a tumor-bearing animal it is theorized, TCF can be freed again to do its work of killing tumor cells. If TCF is added along with DPF the necrosis of tumor tissue can be made to proceed at a more rapid rate. Thus, the essence of tumor treatment according to the principles discovered by the inventors, is to administer TCF and/or DPF to thereby provide free TCF capable of necrosizing the tumorous tissue.

These principles can be used to cause neoplasmic growth (in test animals for experimental purposes), or to detect, destroy or prevent it. Detection of a healthy, remissive or tumorous condition is accomplished by analyzing the blood of the animal for the three main components and comparing a profile of these components with that of a healthy animal. Profiles of healthy, remissive and tumorous animals are distinctive and the comparison indicates the presence or absence of tumors. Furthermore, the profiles of cancerous animals are virtually identical irrespective of animal species.

Accordingly, it is one object of the present invention to provide a method of extracting TCF from mammalian blood without significantly altering or modifying the material from its in vivo condition.

It is a further object to provide a mamalian blood component which is active as an anti-tumor agent.

PREFERRED EMBODIMENTS

The following Table shows the steps which can be employed to isolate TCF from mammalian blood.

TABLE

| Step No. | Sediment No. | Supernatant No. | Description |
|---|---|---|---|
| 1 | | | Cancer Donor Clot in Buffer |
| | | | ↓ Homogenize |
| | | | HOMOGENATE |
| 2 | | | Centrifuge |
| | 1 | 1 | sediment    supernatant fluid |

TABLE-continued

| Step No. | Sediment No. | Supernatant No. | Description |
|---|---|---|---|
| 3 | | | centrifuge |
| 4 | 2 | 2 | sediment    supernatant fluid |
| | | | centrifuge |
| 5 | 3 | 3 | sediment    supernatant fluid |
| | | | Centrifuge |
| | 4 | 4 | sediment    supernatant fluid |
| 6 7 8 9 | | | Resuspend with Buffer Titrate to pH 10.75 Mix for 10 minutes Centrifuge |
| | 5 | 5 | sediment    supernatant fluid |
| 10 11 12 | | | titrate to pH 11.4 mix for 10 minutes Centrifuge |
| | 6 | 6 | sediment    supernatant fluid |
| 13 14 | | | heat Centrifuge |
| | 7 | 7 | sediment    supernatant fluid |
| 15 16 17 | | | heat cool Centrifuge |
| | 8 | 8 | sediment    supernatant fluid |
| 18 19 20 | | | Resuspend in buffer Ampulate and sterilize Assay for activity |

The foregoing will be described in greater detail, each step, sediment and supernatant being identified with the reference numerals given in the table.

The cancer donor clot in buffer suspension which is used as a starting material is derived by suspending a blood clot in buffer solution. The blood clot, which may be pooled samples from different animals of the same species is the cellular portion of untreated (no anticoagulant) whole dated blood separated from the serum portion.

The buffer solution used in any of the following procedures where a buffer is employed is an alkaline buffer such as 0.05M $Na_2HPO_4$ having a pH of 9.2. About 4 parts of buffer are used for each part of clot.

In Step 1, the clot suspension is homogenized. High speed homogenization for several (e.g. 5 minutes) at room temperature effects the desired degree of homogenization.

In Step 2, the resultant homogenizate is centrifuged from 5400 – 10,000g (e.g. at 6500g) for 10 minutes at room temperature to separate cellular debris, fibrinogen and intact red cells from remaining supernatant fluid 1.

In Step 3, supernatant fluid 1 is centrifuged under the conditions of Step 2 to assure complete separation of all the debris, fibrinogen and red cells and the resultant supernatant fluid 2 is then centrifuged in Step 4 at 20,000 to 25,000g (e.g. at 23,500g) for 15 minutes at 0° C. to give sediment 3 and supernatant fluid 3.

Sediment 3 is not employed in the ensuing steps, but it is a useful material and may be retained. This sediment contains BPF and may be used as a source thereof. In addition, this sediment may be used as a basis for a tumor cell assay method, since the concentration of BPF is an indication of the presence or absence of tumor cells in the original blood material.

Supernatant fluid 3, a clear, red liquid rich in TCF is centrifuged in Step 5 at 25,000 to 30,000g. (e.g. at 27,500g) for 20 minutes at 0° C.

In Step 6, the resultant sediment 4 is resuspended with buffer (4× the volume of the original clot), the suspension is titrated to a high alkaline pH (over 10, e.g. pH 10.75) with NH$_4$OH(28%) to denature (Step 7,) the denatured material is mixed for 10 minutes in a vortex mixer (Step 8); and the mixed material is centrifuged at between 22.5 and 30 × 10$^3$g. (e.g. at 22.9 × 10$^3$g.) for one hour at 0° C. (Step 9) giving supernatant fluid 5, and a small amount of sediment 5.

Supernatant fluid 5 is titrated to a pH over 11 with 28% NH$_4$OH (Step 10), mixed for 10 minutes in a vortex mixer (Step 11) and centrifuged at 35 – 42 × 10$^3$g. (e.g. at 40 × 10$^3$g.) for 30 minutes (Step 12) giving supernatant fluid 6. The latter is denatured by heating to 55° – 60° C. for 5 to 10 minutes (Step 13) and the resultant suspension of colloidal polypeptide is centrifuged at 25 – 30 × 10$^3$g. (e.g. at 27.5 × 10$^3$g.) for 5 to 10 minutes (Step 14).

The resultant supernatant fluid 7 is again heated for 10 minutes to 55° – 60° C. (Step 15); cooled on an ice bath for 10 – 20 minutes to 10° – 14° C. (Step 16) to cause agglomeration of colloidal particles and centrifuged at 25 – 30 × 10$^3$g. (e.g. 27,500g.) for 15 to 30 minutes (e.g. for 20 minutes) (Step 17) to cause sedimentation of the agglomerated particles.

The TCF concentration is determined spectrographically. A 3 ml sample of resuspended TCF sediment 8 is exposed in a spectrophotometer (Beckmann ACTA V) between 340 and 279 mm inclusive. The reading at 240 is subtracted from the reading at 194.4 to give absorbance units of TCF per ml. Generally TCF concentration will range from 900 – 5000 absorbance units/ml. If the concentration is 1000 or below, it can be used as such as a tumor necrosis agent. If it is above 1000 it should be diluted with buffer to the activity level of 1000 units/ml.

Resultant sediment 8 is TCF and it is resuspended in buffer (2 × volume of clot), ampulated, sterilized and assayed to determine TCF activity.

Subcutaneous or intramuscular administration of TCF to tumor bearing animals at the ratio of 7 units of TCF to one unit of BPF in 1 ml. of animal's blood when administered in conjunction with a specific titre of DPF results in the onset of tumor necrosis. In C3Ht mice with indurated mammary tumors, the tumors became soft, boggy and approximately ⅛ to 1/10 their original size.

The number of absorbance units is determined spectrophotometrically. The absorbance at 240 nm is subtracted from the absorbance at 199.4 nm. This difference equals the total absorbance of 1 ml. of isolate. An aliquot of this sample is diluted with alkaline buffer so that the absorbance unit content equals 1 absorbance/1ml of isolate. This is serially diluted 50,000 – 100,000 fold and 0.5 ml of this dilution is mixed with 0.5 ml of a standard BPF (105 units). This mixture, after incubation, is titrated for the BPF unit content. If there is a decreased BPF unit content, the units of BPF remaining is subtracted from the standard BPF content (105 units). The difference is divided by 7 since repeated tests (>100) indicated that 7 units of BPF are antagnostic to 1 unit of TFC. Multiplication of this resultant figure by the dilution factor gives the TCF content of 1 absorbance. This product when multiplied by the total absorbance in 1 ml of TCF yields the unit content in total ml. of TCF yield. The method for assaying BPF is disclosed in the application, referred to above, relating to Blocking Protein Fraction.

What is claimed is:

1. A process for the isolation of TCF which comprises:
   (a) suspending in an alkaline buffer a blood clot from an animal having cancer
   (b) homogenizing the resultant suspension to give an homogenizate
   (c) centrifuging the resultant homogenizate at 5400 – 10,000g to get a first supernatant
   (d) centrifuging the first supernatant at 5400 – 10,000g to give a second supernatant
   (e) centrifuging the second supernatant at 20,000 – 25,000g to give a third supernatant
   (f) centrifuging the third supernatant at 25,000 – 30,000g to give a first sediment
   (g) suspending the first sediment in a highly alkaline medium and centrifuging at 22.5 – 30 × 10$^3$g to give a fourth supernatant
   (h) titrating the fourth supernatant with an alkaline material to raise the pH to over 11 and centrifuging the resultant material at 35 – 42 × 10$^3$g giving a fifth supernatant
   (i) heating the fifth supernatant to 55° – 60° C. and centrifuging the resultant colloidal polypeptide at 25 – 30 × 10$^3$g giving a sixth supernatant, and
   (j) heating the sixth supernatant to 55° – 60° C. and cooling the resultant material to cause agglommeration of the resultant TCF particles.

2. The process of claim 1 wherein the centrifuging in step (c) is conducted at 6500 g.

3. The process of claim 1 wherein the centrifuging in step (d) is conducted at 6500 g.

4. The process of claim 1 wherein the centrifuging in step (e) is conducted at 23,500 g.

5. The process of claim 1 wherein the centrifuging in step (f) is conducted at 27,500 g.

6. The process of claim 1 wherein the centrifuging in step (g) is conducted at 27.5 × 10$^3$g.

7. The process of claim 1 wherein the centrifuging in step (h) is conducted at 40 × 10$^3$g.

8. The process of claim 1 wherein the centrifuging in step (i) is conducted at 27.5 × 10$^3$g.

9. A process for the isolation of TCF which comprises:
   (a) suspending in an alkaline buffer, a blood clot from an animal having cancer;
   (b) homogenizing the resultant suspension to give an homogenizate;
   (c) centrifuging the resulting homogenizate at 6500 g. to get a first supernatant;
   (d) centrifuging the first supernatant at 6500 g to give a second supernatant;
   (e) centrifuging the second supernatant at 23,500 g. to give a third supernatant;
   (f) centrifuging the third supernatant at 27,500 g. to give a first sediment;
   (g) suspending the first sediment in the highly alkaline medium and centrifuging at 22.9 × 10$^3$g.;
   (h) titrating the fourth supernatant with an alkaline material to raise the pH to over 11 and centrifuging the resultant material at 40 × 10³ g. giving a fifth supernatant;

(i) heating the fifth supernatant to 55° C. and centrifuging the resultant colloidal polypeptide at 27 × 10³ g. giving a sixth supernatant; and, (j) heating the sixth supernatant to 55° C. and cooling the resulting material to cause agglommeration of the resultant TCF particles.

10. The product produced by the process of claim 1.

11. The product produced by the process of claim 9.

* * * * *